(12) United States Patent
Wolff et al.

(10) Patent No.: US 7,396,919 B1
(45) Date of Patent: Jul. 8, 2008

(54) CHARGE REVERSAL OF POLYION COMPLEXES

(75) Inventors: Jon A. Wolff, Madison, WI (US); Vladimir S. Trubetskoy, Madison, WI (US); Aaron G. Loomis, Stoughton, WI (US); Paul M. Slattum, Madison, WI (US); Sean D. Monahan, Madison, WI (US); James E. Hagstrom, Madison, WI (US); Vladimir G. Budker, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 0 days.

(21) Appl. No.: 09/328,975

(22) Filed: Jun. 9, 1999

Related U.S. Application Data

(60) Provisional application No. 60/093,153, filed on Jul. 17, 1998.

(51) Int. Cl.
*C07H 21/04* (2006.01)
*C12N 15/00* (2006.01)

(52) U.S. Cl. .................... 536/23.1; 435/455

(58) Field of Classification Search .............. 514/44; 435/320.1; 536/23.5, 23.1; 424/484, 486; 436/23.5; 530/350
See application file for complete search history.

(56) References Cited

U.S. PATENT DOCUMENTS

| | | | | |
|---|---|---|---|---|
| 4,049,595 | A * | 9/1977 | Dominguez | 524/426 |
| 5,545,423 | A * | 8/1996 | Soon-Shiong et al. | 424/484 |
| 5,547,932 | A * | 8/1996 | Curiel et al. | 435/456 |
| 5,656,611 | A * | 8/1997 | Kabanov et al. | 514/44 |
| 5,908,777 | A * | 6/1999 | Lee et al. | 435/320.1 |
| 6,339,067 | B1 * | 1/2002 | Wolff et al. | 514/44 |
| 6,740,336 | B2 * | 5/2004 | Trubetskoy et al. | 424/450 |
| 6,740,643 | B2 * | 5/2004 | Wolff et al. | 514/44 |
| 6,818,626 | B1 * | 11/2004 | Wolff et al. | 514/44 |
| 6,881,576 | B2 * | 4/2005 | Wolff et al. | 435/458 |

FOREIGN PATENT DOCUMENTS

WO    WO 97/00965    * 1/1997

OTHER PUBLICATIONS

Verma et al. Nature 389: 239-242 , especially p. 239, Sep. 1997.*
Orkin (Report and Recommendations of the Panel to Assess the NIH Investment in Research on Gene Therapy, see p. 1, item 3, and p. 9, Dec. 1995.*
Anderson et al. Nature 392: 25-30, especially pp. 25 and 30, Apr. 1998.*
Nicolau et al (Biochim. Biophys. Acta 721(2): 185-190, See abstract; p. 187, col. 2, lines 3 and 4 of first full paragraph; and Table 1, p. 188, section A of Table 1, Oct. 1982.*
Vitiello et al Gene Therapy 3(5): 396-404, see abstract, May 1996.*
Baker et al (Nucl. Acids Res. 25(10): 1950-1956, see last sentence of abstract, May 1997.*
Boussif et. al.; A versatile vector for gene and oligonucleotide transfer into cells in culture and in vivo: Polyethylenimine, 1995, Proc. Natl. Acad. Sci. vol. 92: 7297-7301.*
Joel M. Kupfer et al., Human Gene Therapy, 5: pp. 1437-1443 (Dec. 1994).*
L. Gao et al., Human Gene Therapy, 4; pp. 17-24 (1993).*
Patrick Erbacher et al., Drug Delivery, 4: pp. 173-179 (1997).*
Christian Plank et al., The Journal of Biological Chemistry, vol. 269, No. 17, Apr. 29, 1994, pp. 12918-12924.*
Satoshi Katayose et al., Bioconjugate Chem. 1997, 8, pp. 702-707.*
Richards et al (J. Chromatog. (1997) 690(1-2): 43-54).*
GenBank Accession No. AAB22049 (May 7, 1993).*
1998 Promega Catalog, p. 245.*
1995 New England BioLabs Catalog, p. 186.*
Christens-Barry et al (Biopolymers (1989) 28(9): 1515-1526).*
Baker et al (Gene Therapy 4:773-782, Jul. 31, 1997).*
Degols et al (Nucl. Acids Res. 19(4): 945-948, 1991).*
Leonetti et al (J. Nat. Cancer Inst. 88(7): 419-429, 1996).*
Wiethoff et al (J. Biol. Chem. 276(35): 32806-32813, 2001).*
Wu et al (J. Biol. Chem. 269(29): 14621-14624, 1988).*
Livnah O et al. "Three-dimensional structures of avidin and the avidin-biotin complex," Proc. Natl. Acad. Sci. USA; 1993 vol. 90 pp. 5076-5080.
Weber PC et al. "Structural origins of high-affinity biotin binding to streptavidin," Science; 1989 vol. 243 pp. 85-88.
Pugliese L et al. "Three-dimensional structure of the tetragonal crystal form of egg-white avidin in its function complex with biotin at 2.7 A resolution," J Molecular Biol; 1993 vol. 231, No. 3, pp. 698-710.
Bloomfield, V., "DNA Condensation." *Current Opinion in Structural Biology* 1996; 6; 334-341.
Dash, P. Et al., "Factors Affecting Blood Clearance and In Vivo Distribution of Polyelectrolyte Complexes for Gene Delivery." *Gene Therapy* 1999; 6; 643-650.
Dash, P. Et Al., "Synthetic Polymers For Vectorial Delivery of DNA: Characterisation of Polymer-DNA Complexes by Photon Correlation Spectroscopy and Stability to Nuclease Degradation and Disruption by Polyanions in Vitro." *Journal of Controlled Release* 1997; 48; 269-276.
Haensler, J. Et al., "Polyamidoamine Cascade Polymers Mediate Efficient Transfection of Cells in Culture." *Bioconjugate Chemistry* 1993; 4; 372-379.

(Continued)

*Primary Examiner*—Richard Schnizer
(74) *Attorney, Agent, or Firm*—Mark K. Johnson; Kirk Ekena

(57) ABSTRACT

An ionic polymer is utilized in "recharging" (another layer having a different charge) a condensed polynucleotide complex for purposes of nucleic acid delivery to a cell. The resulting recharged complex can be formed with an appropriate amount of positive or negative charge such that the resulting complex has the desired net charge.

1 Claim, 6 Drawing Sheets

OTHER PUBLICATIONS

Hansma, H. Et al., "DNA Condensation for Gene Therapy as Monitored By Atomic Force Microscopy." *Nucleic Acids Research* 1998; vol. 26, No. 10; 2481-2487.

Kabanov, A. Et al., "Interpolyelectrolyte and Block Ionomer Complexes for Gene Delivery: Physico-chemical Aspects." *Advanced Drug Delivery Reviews* 1998; 30; 49-60.

Kichler, A. Et al., "Influence of Membrane-Active Peptides on Lipospermine/DNA Complex Mediated Gene Transfer." *Bioconjugate Chem.* 1997; 8; 213-221.

Maruyama, A. Et et al., "Nanopartical DNA Carrier with Poly)L-lysine) Grafted Polysaccharide Copolymer and Poly(D,L-lactic acid)." *Bioconjugate Chemistry*(1997) 8; 735-42.

Ogris, M. Et al., "PEGylated DNA/Transferrin-PEI Complexes: Reduced Interaction with Blood Components, Extended Circulation in Blood and Potential for Systemic Gene Delivery." *Gene Therapy* 1999; 6; 595-605.

Plank, C. Et al., "The Influence of Endosome-disruptive Peptides on Gene Transfer Using Synthetic Virus-like Gene Transfer Systems." *The Journal of Biological Chemistry* Apr. 29, 1994; vol. 269, No. 17; 12918-12924.

Talingting, M.R. Et al., "Cationic Copolymer Micelles and Anionic Polyelectrolytes Forming Onion-Type Micelles." *Polymer Preprints* 1999; vol. 40, No. 2; 240-241.

Tang, MX, Et al., "The Influence of Polymer Structure on the Interactions of Cationic Polymers with DNA and Morphology of the Resulting Complexes." *Gene Therapy* 1997; 4; 823-832.

Trubeskoy, V. Et al., "Layer-by-Layer Deposition of Oppositely Charged Polyelectrolytes on the Surface of Condensed DNA Particles." *Nucleic Acids Research* 1999; vol. 27, No. 15; 3090-3095.

Trubetskoy, V. Et al., "Quantitative Assessment of DNA Condensation." *Analytical Biochemistry* 1999; 267; 309-313.

Wolfert, M. Et al., "Characterization of Vectors for Gene Formed by Self-Assembly of DNA with Synthetic Block Co-Polymers." *Human Gene Therapy* Nov. 10, 1996; 7; 2123-2133.

Xu, Y. Et al., "Mechanism of DNA Release From Cationic Liposome/DNA Complexes Used in Cell Transfection." *Biochemistry* 1996; 35; 5616-5623.

* cited by examiner

Amount of polyanion added, ug

US 7,396,919 B1

CHARGE REVERSAL OF POLYION COMPLEXES

CROSS-REFERENCE TO RELATED APPLICATIONS

| (Provisional Application Serial No.) | (Filing Date) |
|---|---|
| 60/093,153 | Jul. 17, 1998 |

FEDERALLY SPONSORED RESEARCH

N/A

FIELD OF THE INVENTION

The invention relates to compounds and methods for use in biologic systems. More particularly, polyions are utilized for reversing the charge ("recharging") particles, such as molecules, polymers, nucleic acids and genes for delivery to cells.

Background Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective. The following are some principles involving the mechanism by which polycations facilitate uptake of DNA:

Polycations provide attachment of DNA to the target cell surface. The polymer forms a cross-bridge between the polyanionic nucleic acids and the polyanionic surfaces of the cells. Polycations protect DNA in complexes against nuclease degradation. Polycations can also facilitate DNA condensation. The volume which one DNA molecule occupies in a complex with polycations is drastically lower than the volume of a free DNA molecule. The size of a DNA/polymer complex is important for gene delivery in vivo.

In terms of intravenous injection, DNA must cross the endothelial barrier and reach the parenchymal cells of interest. The largest endothelia fenestrae (holes in the endothelial barrier) occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20-30 nm. The size of the DNA complexes is also important for the cellular uptake process. After binding to the target cells the DNA-polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized. 2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

Depending upon the concentration of DNA, condensation leads to three main types of structures:

1) In extremely dilute solution (about 1 microgram/mL or below), long DNA molecules can undergo a monomolecular collapse and form structures described as toroid. 2) In very dilute solution (about 10 micrograms/mL) microaggregates form with short or long molecules and remain in suspension. Toroids, rods and small aggregates can be seen in such solution. 3) In dilute solution (about 1 mg/mL) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids similar in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not clear. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In a case of DNA-polymeric polycation interactions, DNA condensation is a more complicated process than the case of low molecular weight polycations. Different polycationic proteins can generate toroid and rod formation with different size DNA at a ratio of positive to negative charge of 0.4. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations.

The electrophoretic mobility of DNA-polycation complexes can change from negative to positive in excess of polycation. It is likely that large polycations don't completely align along DNA but form polymer loops that interact with other DNA molecules. The rapid aggregation and strong intermolecular forces between different DNA molecules may prevent the slow adjustment between helices needed to form tightly packed orderly particles.

Cationic molecules with charge greater than +2 are able to condense DNA into compact structures (Bloomfield V. A., DNA condensation, (1996) Curr, Opion in Struct. Biol., 6:334-341). This phenomenon plays a role in chromatin and viral assembly and is of particular importance in the construction of artificial gene delivery vectors. Morphologies of condensed DNA during titration of DNA with polycations are now well documented. When DNA is in excess (DNA/polycation charge ratio >1), complexes assemble into "daisy-shaped" particles that stabilized with loops of uncondensed DNA (Hansma, G. H., Golan, R., Hsieh, W., Lollo, C. P., Mullen-Ley, P. and Kwoh. D. (1998) DNA condensation for gene therapy as monitored by atomic force microscopy, Nucleic Acids Res. 26:2481-2487). When polycation is in excess (DNA/polycation ratio <1), DNA condenses completely within particles that adopt customarily toroid morphology (Tang, M. X., and Szoka, F. C., Jr. 1997, The influence of polymer structure on the interactions of cationic polymers with DNA and morphology of the resulting complexes, Gene Ther. 4:823-832). In low salt aqueous solutions the excess of polycation stabilizes these highly condensed structures and maintains them in soluble state (Kabanov A V, Kabanov V A., Interpolyelectrolyte and block ionomer complexes for gene delivery: physico-chemical aspects, Adv. Drug Delivery Rev. 30:49-60 (1998)).

Several methods can be used to determine the condensation state of DNA. They include the prevention of fluorescent molecules such as ethidium bromide from intercalating into the DNA. The condensation state of DNA was monitored as previously described (Dash, R R, Toncheva V, Schacht E, Seymour L W J. Controlled Release 48:269-276). Alternatively the condensation of fluorescein-labeled DNA (or any fluorescent group) causes self-quenching by bringing the fluorescent groups on the DNA closer together (Trubetskoy, V S, Budker, V G, Slattum, P M, Hagstrom, J E and Wolff, J A. Analytical Biochemistry 267:309-313, 1999).

Preparation of Negatively-Charged (Anionic) Particles

As previously stated, preparation of polycation-condensed DNA particles is of particular importance for gene therapy, more specifically, particle delivery such as the design of non-viral gene transfer vectors. Optimal transfection activity in vitro and in vivo can require an excess of polycation molecules. However, the presence of a large excess of polycations may be toxic to cells and tissues. Moreover, the non-specific binding of cationic particles to all cells forestalls cellular targeting. Positive charge also has an adverse influence on biodistribution of the complexes in vivo.

SUMMARY

In order to avoid unwanted effects, anionic particles containing an excess of DNA and cell receptor ligands for targeting have been developed. The present invention describes a process for negatively charging DNA particles by recharging fully condensed polycation/DNA complexes with polyions.

In a preferred embodiment, a process is described for delivering a complex to a cell, comprising, forming a compound having a net charge comprising a polyion and a polymer in a solution, adding a charged polymer to the solution in sufficient amount to form the complex having a net charge different from the compound net charge; and, inserting the complex into a mammal.

In another preferred embodiment, a complex for delivering a polyion to a cell, is described, comprising a polyion and a charged polymer wherein the polyion and the charged polymer are bound in complex, the complex having a net charge that is the same as the net charge of the charged polymer.

In another preferred embodiment a drug for delivery to a cell, is described, comprising a polycation non-covalently attached to a polyanion complexed with a negatively charged polyion.

Reference is now made in detail to the preferred embodiments of the invention, examples of which are illustrated in the accompanying drawings.

DETAILED DESCRIPTION

Figure 1A:
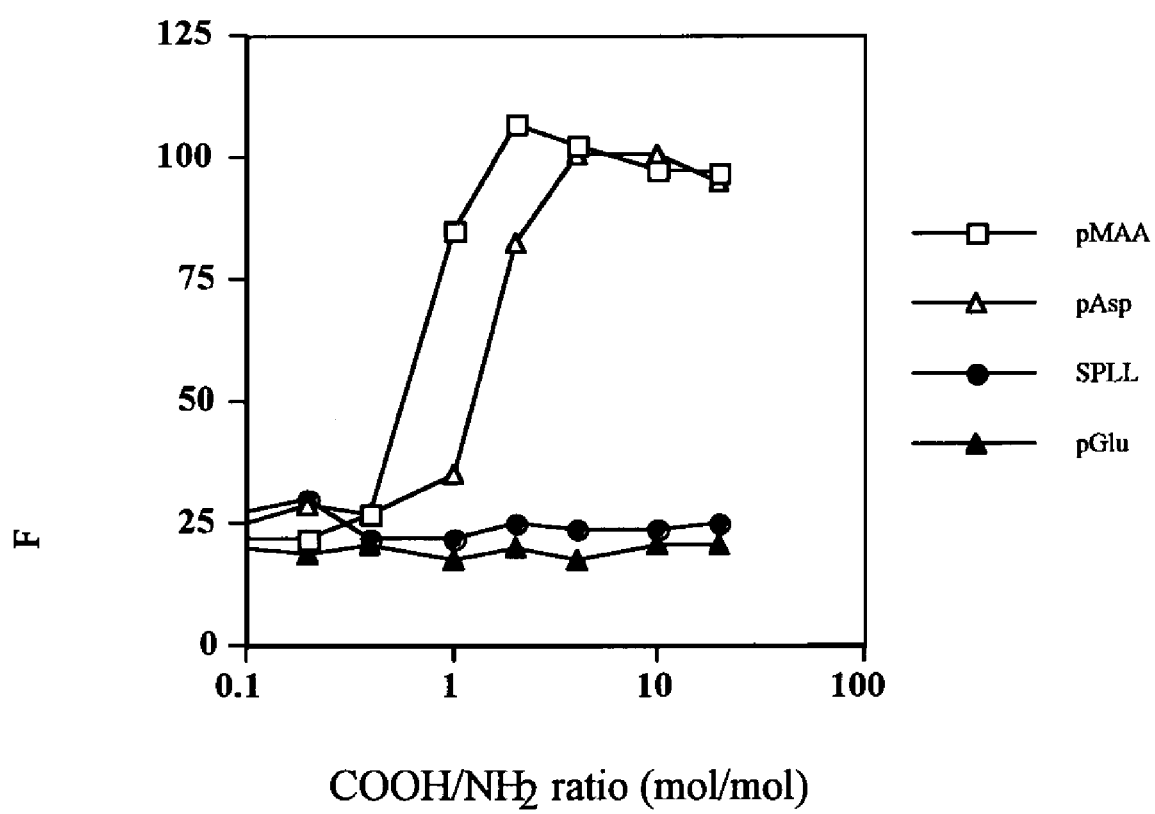
FIG. 1(A) illustrates Fl-DNA decondensation during titration of Fl-DNA/PLL complex (1:3 charge ratio, (Fl-DNA) =20 μg/ml, 25 mM HEPES, pH 7.5) with different polyanions; (B) titration of DNA/PLL (1:3 charge ratio, (DNA)=20 μg/ml, 25 mM HEPES, pH 7.5) complex with SPLL as assessed by light scattering methods. Intensity of scattered light (I90) was measured using spectrofluorimeter. Percentage of particles <100 nm in diameter was measured using particle size analyzer as described in the specification. COOH/NH2 ratios were calculated on the basis of mol weights of N-succinyl lysine and lysine monomers in SPLL and PLL respectively; (C) potential changes during titration of DNA/PLL complex (1:3 charge ratio, (DNA)=20 micrograms/ml, 25 mM HEPES, pH 7.5) with SPLL.

Abbreviations: Poly-L-Lysine (PLL), succinic anhydride-PLL (SPLL), polymethacrylic acid, pMAA and polyaspartic acid, pAsp Gene therapy research may involve the biological pH gradient that is active within organisms as a factor in delivering a polynucleotide to a cell. Different pathways that may be affected by the pH gradient include cellular transport mechanisms, endosomal disruption/breakdown, and particle disassembly (release of the DNA).

Gradients that can be useful in gene therapy research involve ionic gradients that are related to cells. For example, both Na+ and K+ have large concentration gradients that exist across the cell membrane. Recharging systems can utilize such gradients to influence delivery of a polynucleotide to a cell. DNA can be compacted by adding polycations to the mixture. By interacting an appropriate cation with a DNA containing system, DNA condensation can take place. Since the ion utilized for compaction may exist in higher concentration outside of the cell membrane compared to inside the cell membrane, this natural ionic gradient can be utilized in delivery systems.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-

Or the other approach is to have two difunctional monomers.

A-A+B-B yields -[A-A-B-B]-

Generally, these reactions can involve acylation or alkylation. Acylation is defined as the introduction of an acyl group (—COR) onto a molecule. Alkylation is defined as the introduction of an alkyl group onto a molecule.

"If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, or acid halide, p-nitrophenyl ester, o-nitrophenyl ester, pentachlorophenyl ester, pentafluorophenyl ester, carbonylimidazole, carbonyl pyridinium, or carbonyl dimethylaminopyridinium. In other terms when function A is an amine then function B can be acylating or alkylating agent or amination agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) adiazoacetate or an amine in which a carbodiimide is used. Other additives may be utilized such as carbonyldiimidazole, dimethylamino pyridine (DMAP), N-hydroxysuccinimide or alcohol using carbodiimide and DMAP.

If functional group A is an hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one bifunctional monomer so that A-A plus another agent yields -[A-A]-. If function A is a sulfhydryl group then it can be converted to disulfide bonds by oxidizing agents such as iodine (I2) or NaIO4 (sodium periodate), or oxygen (O2). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation. Functional group A or B in any of the above examples could also be a photoreactive group such as aryl azide (including halogenated aryl azide), diazo, benzophenone, alkyne or diazirine derivative.

Reactions of the amine, hydroxyl, sulfhydryl, carboxylate groups yield chemical bonds that are described as amide, amidine, disulfide, ethers, esters, enamine, imine, urea, isothiourea, isourea, sulfonamide, carbamate, alkylamine bond (secondaryamine), carbon-nitrogen single bonds in which the carbon contains a hydroxyl group, thioether, diol, hydrazone, diazo, or sulfone".

If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one difunctional monomer so that

A-A plus another agent yields -[A-A]-.

If function A is a sulfhydryl group then it can be converted to disulfide bonds by oxidizing agents such as iodine (I2) or NaIO4 (sodium periodate), or oxygen (O2). Function A can also be an amine that is converted to a sulfhydryl group by reaction with 2-iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methaacrylamide groups can undergo chain reaction which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Peptide refers to a linear series of amino acid residues connected to one another by peptide bonds between the alpha-amino group and carboxyl group of contiguous amino acid residues. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Reporter or marker molecules are compounds that can be easily detected. Typically they are fluorescent compounds such as fluorescein, rhodamine, texas red, CY-5, CY-3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

Signals

In a preferred embodiment, a chemical reaction can be used to attach a signal to a nucleic acid complex. The signal is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The signal can be a protein, peptide, lipid, steroid, sugar, carbohydrate, nucleic acid or synthetic compound. The signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the gene or particle with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

The present invention provides compounds used in systems for the transfer of polynucleotides, oligonucleotides, and other compounds into association with cells within tissues in situ and in vivo.

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The polynucleotides or genetic material being delivered are generally mixed with transfection reagents prior to delivery.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples of biologically active compounds.

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nucleic acid includes deoxyribonucleic acid (DNA) and ribonucleic acid (RNA). DNA may be in the form of antisense, plasmid DNA, parts of a plasmid DNA, vectors (Pl, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. "Anti-sense" is a polynucleotide that interferes with the function of DNA and/or RNA. This may result in suppression of expression. Natural nucleic acids have a phosphate backbone, artificial nucleic acids may contain other types of backbones, nucleotides, or bases. These include PNAs (peptide nucleic acids), phosphothionates, and other variants of the phosphate backbone of native nucleic acids. In addition, DNA and RNA may be single, double, triple, or quadruple stranded. "Expression cassette" refers to a natural or recombinantly produced polynucleotide molecule which is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The term "naked polynucleotides" indicates that the polynucleotides are not associated with a transfection reagent or other delivery vehicle that is required for the polynucleotide to be delivered to the cardiac muscle cell. A "transfection reagent" is a compound or compounds used in the prior art that bind(s) to or complex(es) with oligonucleotides and polynucleotides, and mediates their entry into cells. The transfection reagent also mediates the binding and internalization of oligonucleotides and polynucleotides into cells. Examples of transfection reagents include cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine may be ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. Polyethylenimine, which facilitates gene expression without additional treatments, probably disrupts endosomal function itself.

Other vehicles are also used, in the prior art, to transfer genes into cells. These include complexing the polynucleotides on particles that are then accelerated into the cell. This is termed "biolistic" or "gun" techniques. Other methods include "electroporation." in which a device is used to give an electric charge to cells. The charge increases the permeability of the cell.

Ionic (electrostatic) interactions are the non-covalent association of two or more substances due to attractive forces between positive and negative charges, or partial positive and partial negative charges.

Condensed Nucleic Acids: Condensing a polymer means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism.

A delivered polymer can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Condensed nucleic acids may be delivered intravasculary, intrarterially, intravenously, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. "Delivered" means that the polynucleotide becomes associated with the cell. The polynucleotide can be on the membrane of the cell or inside the cytoplasm, nucleus, or other organelle of the cell.

An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

An administration route involving the mucosal membranes is meant to include nasal, bronchial, inhalation into the lungs, or via the eyes.

Recharging Condensed Nucleic Acids

Polyions for gene therapy and gene therapy research can involve anionic systems as well as charge neutral or charge-positive systems. The ionic polymer can be utilized in "recharging" (another layer having a different charge) the condensed polynucleotide complex. The resulting recharged complex can be formed with an appropriate amount of charge such that the resulting complex has a net negative, positive or neutral charge. The interaction between the polycation and the polyanion can be ionic, can involve the ionic interaction of the two polymer layers with shared cations, or can be crosslinked between cationic and anionic sites with a crosslinking system (including cleavable crosslinking systems, such as those containing disulfide bonds). The interaction between the charges located on the two polymer layers can be influenced with the use of added ions to the system. With the appropriate choice of ion, the layers can be made to disassociate from one another as the ion diffuses from the complex into the cell in which the concentration of the ion is low (use of an ion gradient).

Electrostatic complexes between water-soluble polyelectrolytes have been studied widely in recenty ears. Complexes containing DNA as a polyanionic constituent only recently came to the attention because of their potential use in gene therapy applications such as non-viral gene transfer preparations (polyplexes) for particle delivery to a cell. Strong polyelectrolytes, polyanion/polycation complexes, are usually formed at a 1:1 charge stoichiometrically. A charge ratio 1:1 complex between DNA and Poly-L-Lysine (PLL) also has been demonstrated in the prior art.

Polyanions effectively enhance the gene delivery/gene expression capabilities of all major classes of polycation gene delivery reagents. In that regard, we disclose the formation of negatively charged tertiary complexes containing nucleic acid, PLL, and succinic anhydride-PLL (SPLL) complexes. SPLL is added to a cationic nucleic acid/PLL complex in solution. Nucleic acid at the core of such complexes remains condensed, in the form of particles ~50 nm in diameter. DNA and PLL binds SPLL in 1:1:1 complex with SPLL providing a net negative charge to the entire complex. Such small negatively charged particles are useful for non-viral gene transfer applications.

One of the advantages that flow from recharging DNA particles is reducing their non-specific interactions with cells and serum proteins [(Wolfert et al. Hum. Gene Therapy 7:2123-2133 (1996); Dash et al., Gene Therapy 6:643-650 (1999); Plank et al., Hum. Gene Ther. 7:1437-1446 (1996); Ogris et al., Gene Therapy 6:595-605 (1999); Schacht et al. Brit. Patent Application 9623051.1 (1996)]

A wide a variety of polyanions can be used to recharge the DNA/polycation particles. They include (but not restricted to): Any water-soluble polyanion can be used for recharging purposes including succinylated PLL, succinylated PEI (branched), polyglutamic acid, polyaspartic acid, polyacrylic acid, polymethacrylic acid, polyethylacrylic acid, polypropylacrylic acid, polybutylacrylic acid, polymaleic acid, dextran sulfate, heparin, hyaluronic acid, polysulfates, polysulfonates, polyvinyl phosphoric acid, polyvinyl phosphonic acid, copolymers of polymaleic acid, polyhydroxybutyric acid, acidic polycarbohydrates, DNA, RNA, negatively charged proteins, pegylated derivatives of above polyanions, pegylated derivatives carrying specific ligands, block and graft copolymers of polyanions and any hydrophilic polymers (PEG, poly(vinylpyrrolidone), poly(acrylamide), etc).

These polyanions can be added prior to the nucleic acid complex being delivered to the cell or organism. In one preferred embodiment the recharged nucleic acid complexes (polyanion/polycation/nucleic acid complex) are formed in a container and then administered to the cell or organism. In another preferred embodiment, the polycation/nucleic acid complex is recharged with a polyion prior to delivery to the organism and the nucleic acid remains condensed. In this embodiment the nucleic acid can remain more than 50%, 60%, 70%, 80%, 90% or 100% condensed as well.

When an excess of polyion is present, DNA forms soluble condensed (toroid) structures stabilized with an excess of polyion. When, in addition to this binary complex, a third polyelectrolyte is present, a tertiary complex exists. In the absence of salt such tertiary complex might exist indefinitely. If the last added polyion is in excess, it stabilizes the complex in the form of a soluble colloid. Using this method, a DNA/polycation complex, which maintains a net positive charge, reverses its charge and becomes "recharged". The complex can be designed (e.g. choice of polycation and polyanion, presence of crosslinking) so that in the presence of salt, the complex dissociates into binary complex and free excess of third polyion.

In general, tertiary DNA/PLL/SPLL complex exhibit the same colloid properties as binary DNA/PLL complex. In low salt solution it forms flocculate around PLL/SPLL charge equivalence point (FIG. 1).

DNA condensation assays based on the effect of concentration-dependent self-quenching of covalently-bound fluorophores upon DNA collapse indicated essentially the same phenomenon described in the prior art. Polyanions with high charge density (polymethacrylic acid, pMAA and polyaspartic acid, pAsp) were able to decondense DNA prior to those that complexed with PLL while polyanions with lower charge density (polyglutamic acid, pGlu, SPLL) failed to decondense DNA (FIG. 1). Together with z-potential measurements (FIG. 3), these data represent support for the presence of negatively charged condensed DNA particles. These particles are approximately 50 nm in diameter in low salt buffer as measured by atomic force microscopy (FIG. 2) which revealed particles of spheroid morphology. This places them very close in size to binary DNA/PLL particles.

The issue of stoichiometry in such tertiary complexes is of primary importance to determine how much polyanion is associated with DNA after formation of tertiary complex and potential dissociation of polycation after polyanion binding. We developed a methodology for DNA complex stoichiometry determination which includes step density gradient ultracentrifugation of complexes prepared with fluorescently labeled DNA, PLL and SPLL. Retrieved complexes were always found aggregated and possess DNA/PLL/SPLL (1:1:1) stoichiometry. This surprising finding assumes major redistribution of charges inside the particle since net charge of the complex is negative. Excess PLL was found to complex with any excess SPLL.

In another preferred embodiment, the polyanion can be covalently attached to the polycation using a variety of chemical reactions without the use of crosslinker. The polyanion can contain reactive groups that covalently attach to groups on the polycation. The types of reactions are similar to those discussed above in the section on step polymerization.

In another preferred embodiment the attachment of the recharged complex can be enhanced by using chelators and crown ethers, preferably polymeric.

Excess of the polycations or polyanions can be toxic or interfere with nucleic acid delivery and transfection. In one preferred embodiment the DNA/polycation complexes are initially formed by adding only a small excess of polycation to nucleic acid (in charge ratio which is defined as ratio of polycation total charge to polyanion total charge at given pH). The charge ratio of polycation to nucleic acid charge could be less than 2, less than 1.7, less than 1.5 or even less than 1.3. This would be preferably done in low ionic strength solution so as to avoid the complexes from flocculation. Low ionic strength solution means solution with total monovalent salt concentration less than 50 mM. Then the polyanion is added to the mixture and only a small amount of "blank" particles are formed. "Blank" particles are particles that contain only polycation and polyanion and no nucleic acid.

In another preferred embodiment, the polycation is added to the nucleic acid in charge excess but the excess polycation that is not in complex with the nuclei acid is removed by purificaton. Purification means removing of charged polymer using centrifugation, dialysis, chromatography, electrophoresis, precipitation, extraction.

Yet in another preferred embodiment a ultracentrifugation procedure (termed "centrifugation step") is used to reduce the amount of excess polycation, polyanion, or "blank" particles. The method is based on the phenomenon that only dense DNA-containing particles can be centrifuged through 10% sucrose solution at 25,000 g. After centrifugation purified complex is at the bottom of the tube while excess of polyanion and "blank" particles stay on top. In modification of this experiment 40% solution of metrizamide can be used as a cushion to collect purified DNA/polycation/polyanion complex on the boundary for easy retrieval.

The attachment of the polyanion to the DNA/polycation complex enhance stability but can also enable a ligand or signal to be attached to the DNA particle. This is accomplished by attaching the ligand or signal to the polyanion which in turn is attached to the DNA particle. A dialysis step or centifugation step can be used to reduce the amount of free polyanion containing a ligand or signal that is in solution and not complexed with the DNA particle. One approach is to replace the free, uncomplexed polyanion containing a ligand or signal with free polyanion that does not contain a ligand or signal.

Yet in another preferred embodiment a polyanion used for charge reversal is modified with neutral hydrophilic polymer for steric stabilization of the whole complex. The complex formation of DNA with pegylated polycations results in substantial stabilization of the complexes towards salt- and serum-induced flocculation (Wolfert et al. Hum. Gene Therapy 7:2123-2133 (1996), Ogris et al., Gene Therapy 6:595-605 (1999). We have demonstrated that modification of polyanion in triple complex also significantly enhances salt and serum stability.

In another preferred embodiment a polyanion used for charge reversal is cleavable. One can imagine two ways to design a cleavable polyion: 1. A polyion cleavable in backbone, 2. A polyion cleavable in side chain. First scenario would comprise monomers linked by labile bonds such as disulfide, diols, diazo, ester, sulfone, acetal, ketal, enol ether, enol ester, imine and enamine bonds. Second scenario would involve reactive groups (i.e. electrophiles and nucleophiles) in close proximity so that reaction between them is rapid. Examples include having corboxylic acid derivatives (acids, esters and amides) and alcohols, thiols, carboxylic acids or amines in the same molecule reacting together to make esters, thiol esters, anhydrides or amides. In one specific preferred embodiment the polyion contains an ester acid such as citraconnic acid, or dimethylmaleyl acid that is connected to a carboxylic, alcohol, or amine group on the polyion.

Cleavable means that a chemical bond between atoms is broken. Labile also means that a chemical bond between atoms is breakable. Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule.

EXAMPLES

Example 1

Materials. Plasmid DNA (pCILuc) used for the condensation studies was provided by Bayou Biolabs, Harahan, La. Poly-L-lysine (PLL) (MW 34 kDa), poly-L-aspartic acid (pAsp) (MW 36 kDa), poly-L-glutamic acid (PLG) (MW 49 kDa) and rhodamine B isothiocyanate were products of Sigma (St. Louis, Mo.). Polymethacrylic acid (PMA), metrizamide and fluoresceine isothiocyanate were from Aldrich (Milwaukee, Wis.). LabelIT kits (Mirus Corp., Madison, Wis.) were used for covalent labeling DNA with fluorescein and rhodamine.

Synthesis of succinylated PLL (SPLL). Succinic anhydride (30 mg) dissolved in 150 µl DMSO were added to PLL (20 mg) dissolved in 1 ml of 0.1 M sodium tertraborate solution in two portions. After 10 min incubation at room temperature, the polymer was precipitated with two volumes of isopropanol with subsequent reconstitution with deionized water.

Labeling of PLL and DNA with fluorescein and rhodamine. Fluorescein isothiocyanate (0.37 mg in 5 µl DMSO) was added to PLL (20 mg) in 1 ml of sodium tertraborate and incubated for 1 hr. Resulting Fl-PLL was purified by isopropanol precipitation. Fl-PLL was used also for preparation of Fl-SPLL by succinylation as described above. For DNA labeling, DNA and LabelIT reagent (Mirus Corp., Madison, Wis.) were mixed in HEPES buffer (25 mM HEPES, pH 7.5) in reagent/DNA weight ratios of 1:1 and incubated for 1 hr at 37 C. Labeled DNA was precipitated two times with NaCl/ethanol mixture (final NaCl concentration was 0.2 M, ethanol 66%) and immediately redissolved in deionized water DNA/polyion complex formation. DNA/PLL/SPLL complexes were formed in 25 mM HEPES, pH 7.5 at DNA concentration 20-100 µg/ml. The complex with DNA/PLL charge ratio (1:3) was formed by consecutive addition of PLL and then various amount of SPLL and vortexing for 30 sec.

Light scattering and zeta-potential measurements. Intensity of scattered light measured at 90° angle (I90) was estimated using Shimadzu RF 1501 set at ex=600 nm; em=600 nm. Particle sizing and zeta-potential measurements were performed using a Zeta Plus Particle Analyzer (Brookhaven Instruments Corp., Holtsville, N.Y.), with a laser wavelength of 532 nm.

Atomic force microscopy. Images of DNA particles were obtained using BioProbe AFM microscope (Park Scientific instruments, Sunnyvale, Calif.). Samples (DNA concentration 1 µg/ml in 25 mM HEPES, pH 7.5) were allowed to adsorb on mica in the presence of 1 mM NiCl2 for 5 min and then were viewed in the buffer in a contact mode.

Ultracentrifugation experiments. For stoichiometry studies, tertiary complexes were formed using fluorescently labeled polyions. Two types of complexes were formed in 25 mM HEPES, pH 7.5, (charge ratio 1:3:10): a) Rh-DNA/Fl-PLL/SPLL and b) Rh-DNA/PLL/Fl-SPLL. The samples (1 ml) were layered on top of 10% sucrose solution (10 ml) with 1 ml of 40% metrizamide cushion on the bottom and were centrifuged in SW-41 Beckman rotor in Optima LE-80K ultracentrifuge at 30 000 rpm for 20 min. DNA-containing complexes were retrieved from sucrose/metrizamide boundary using Pasteur pipet and were dissolved in 2.5 M NaCl solution. Visible spectra of the complexes and 1:1 premixed Rh-DNA/Fl-PLL and Rh-DNA/Fl-SPLL standards (700-400 nm) were recorded using Shimadzu UV 1601 spectrophotometer.

Example 2

Figure 1B:
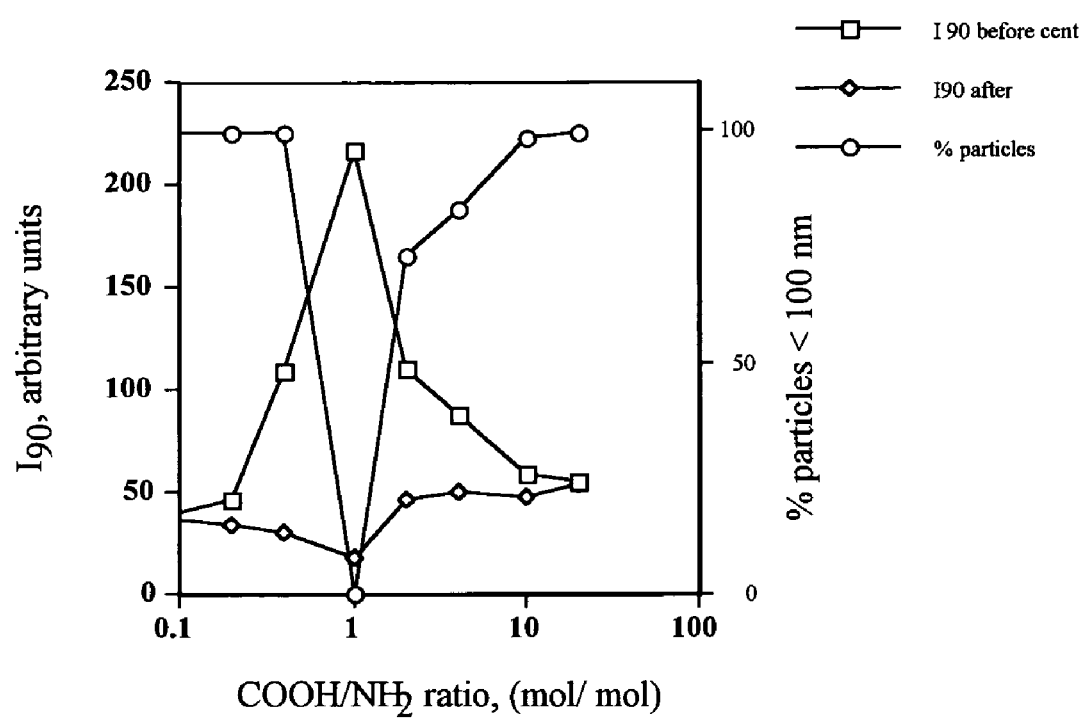

Recharging of Polyion Condensed DNA Particles: The chief DNA/polycation complex used was DNA/PLL (1:3 charge ratio) formed in low salt buffer. At these conditions, plasmid DNA is completely condensed and compacted into toroid-shaped soluble particles stabilized with excess of polyion (Kabanov et al. Adv. Drug Delivery Rev 30:49-60 (1998). The DNA particles were characterized after addition of a third polyion component to such binary DNA/polyion complex. It has been shown that polyanion (polymer or negatively-charged lipid bilayer) can release DNA from its complex with cationic liposomes. As judged by DNA condensation assay based on ethidium bromide binding, upon addition of such polyanions as dextran sulfate or heparin to the DNA/DOTAP lipid complexes results in release of free DNA. Using a fluorescein-labeled DNA condensation assay (Trubetskoy et al. Anal. Biochem. 267:309-313 (1999) we demonstrate that the same is true for DNA/synthetic polyion complexes (FIG. 1A).

The aggregation state of condensed DNA particles was determined using both static and dynamic light scattering techniques. Upon titration of DNA/PLL (1:3) complex with increasing amounts of SPLL in low salt solution, turbidity of the reaction mixture, an indication of aggregation, increases when the lysine to lysyl succinate (NH2/COOH) ratio approaches 1:1 (FIG. 1(B)). With an excess of polyanion, turbidity decreases. Correspondingly, assessment of particle size by dynamic light scattering shows that small DNA particles (<100 nm) exist before and after the equivalent point. Large aggregates are present only at a 1:1 charge ratio of polyion to polyanion.

Figure 1C:
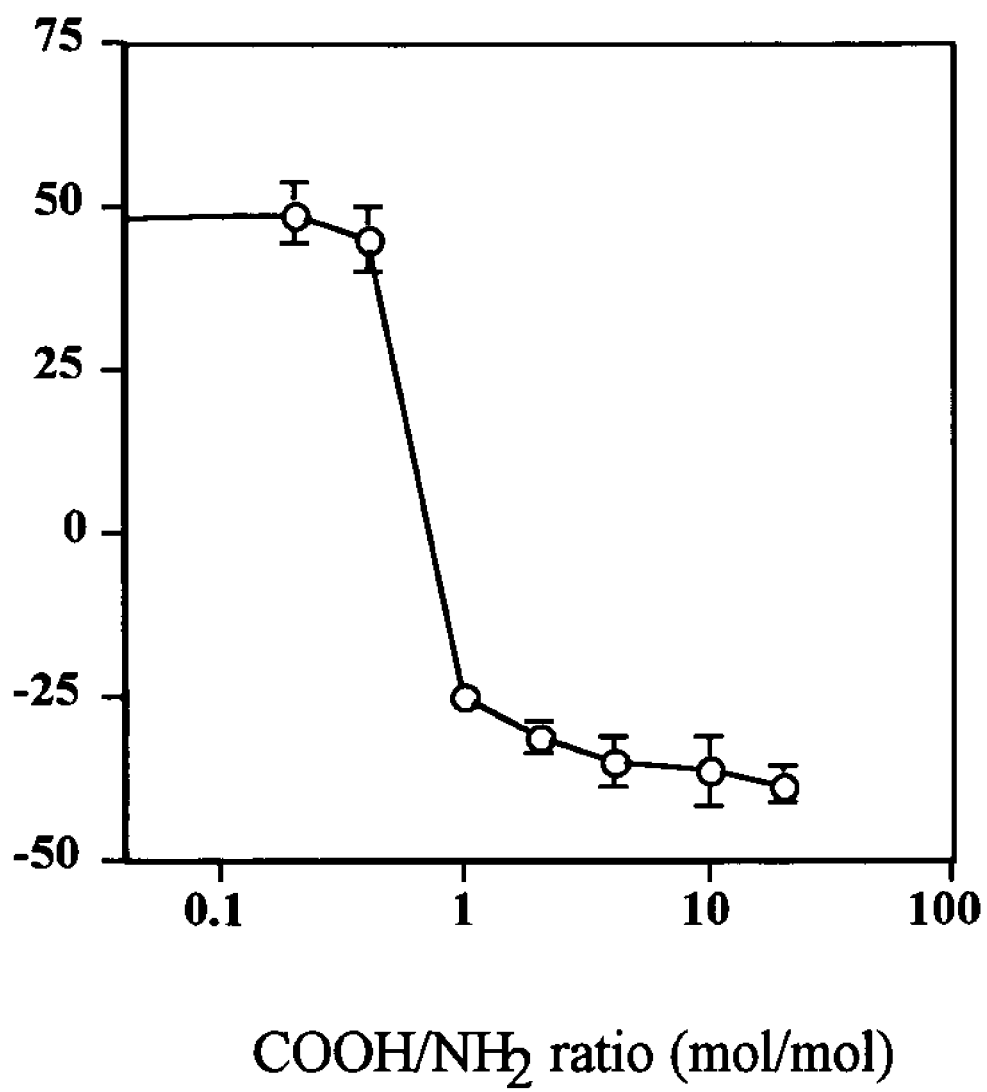

FIG. 1(C) demonstrates the change of particle surface charge (zeta potential) during titration of DNA/PLL (1:3) particles with SPLL. The particle becomes negatively charged and accordingly recharged at approximately the equivalence point (FIG. 1(C)).

Figure 2:
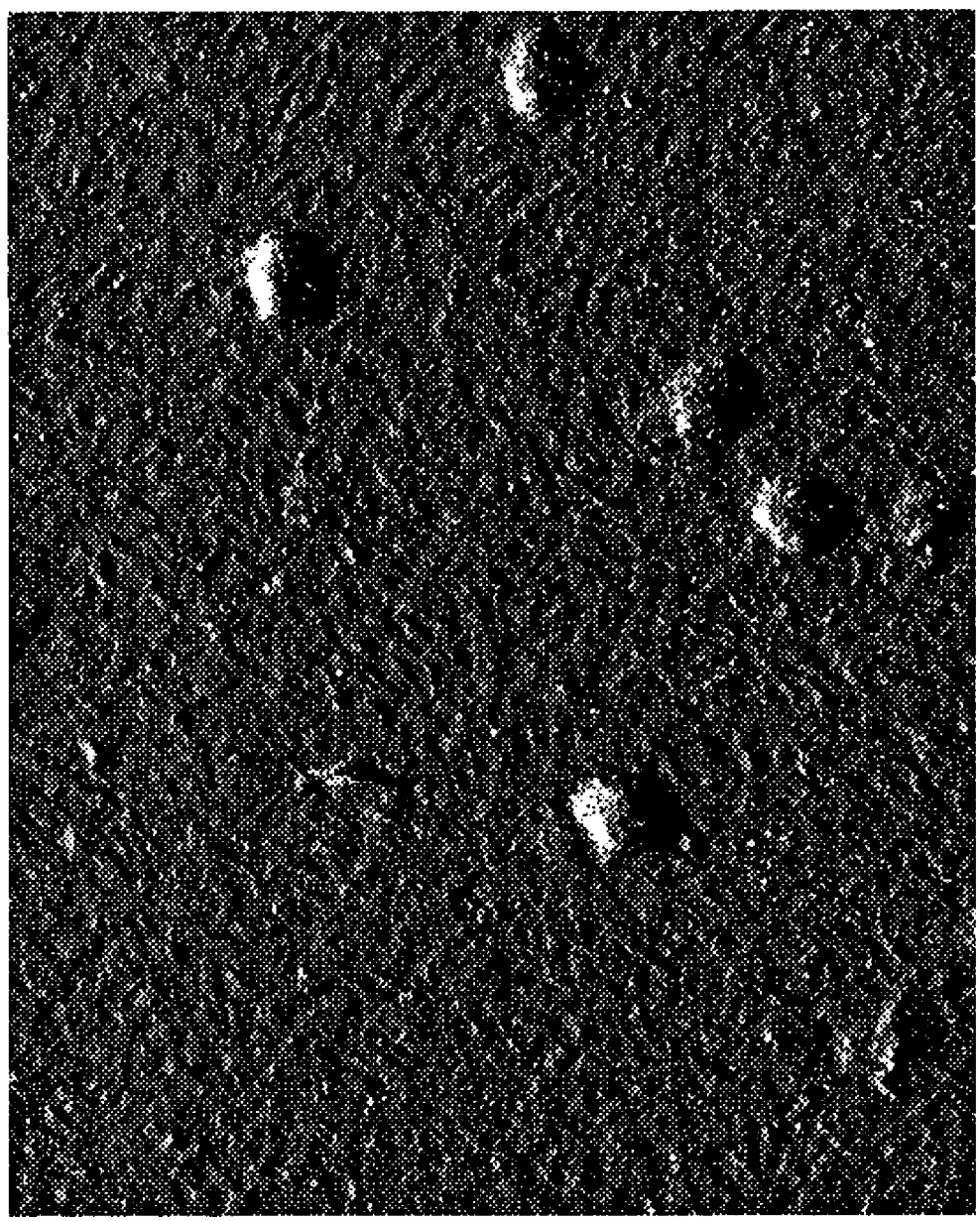
FIG. 2 illustrates AFM images of DNA/PLL/SPLL complexes (1:3:10 initial ratio) absorbed on mica in 25 mM HEPES, pH 7.5 as described in the specification.

Thus, upon addition of large excess of non-decondensing polyanion small non-aggregated particles still exist, DNA is still condensed but the charge of the particles becomes negative. We used atomic force microscopy to visualize these negatively charged particles. FIG. 2 shows small and non-aggregated 50 nm DNA/PLL/SPLL spheroids adsorbed on mica in the presence of 1 mM NiCl2.

Any water-soluble polyanion can be used for recharging purposes including succinylated PLL, succinylated PEI, polyglutamic acid, polyaspartic acid, polyacrylic acid, polymethacrylic acid, dextran sulfate, heparin, hyaluronic acid, DNA, RNA, negatively charged proteins, polyanions graft-copolymerized with hydrophilic polymer, and the same carrying specific ligands.

Example 3

Figure 3A:
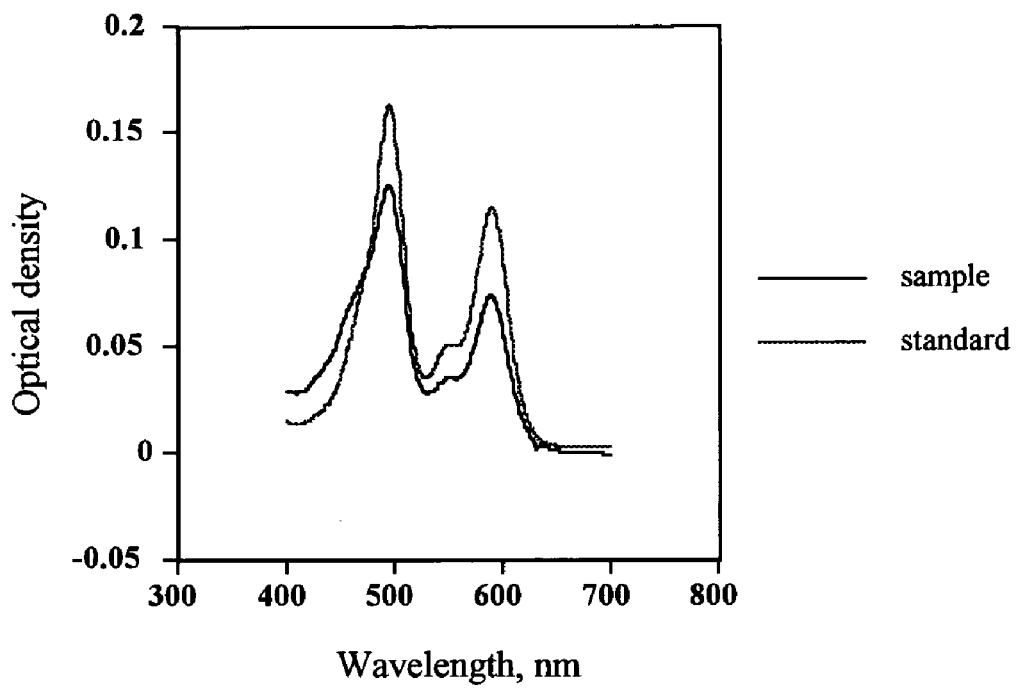
FIG. 3(A) illustrates visible spectra of DNA complexes isolated after Rh-DNA/Fl-PLL/SPLL (1:3:10) ultracentrifugation and Rh-DNA/Fl-PLL (1:1) standard dissolved in 2.5 M NaCl; (B) visible spectra of DNA complexes isolated after Rh-DNA/PLL/Fl-SPLL (1:3:10) ultracentrifugation and Rh-DNA/Fl-SPLL (1:1) standard in the same conditions.
Figure 3B:
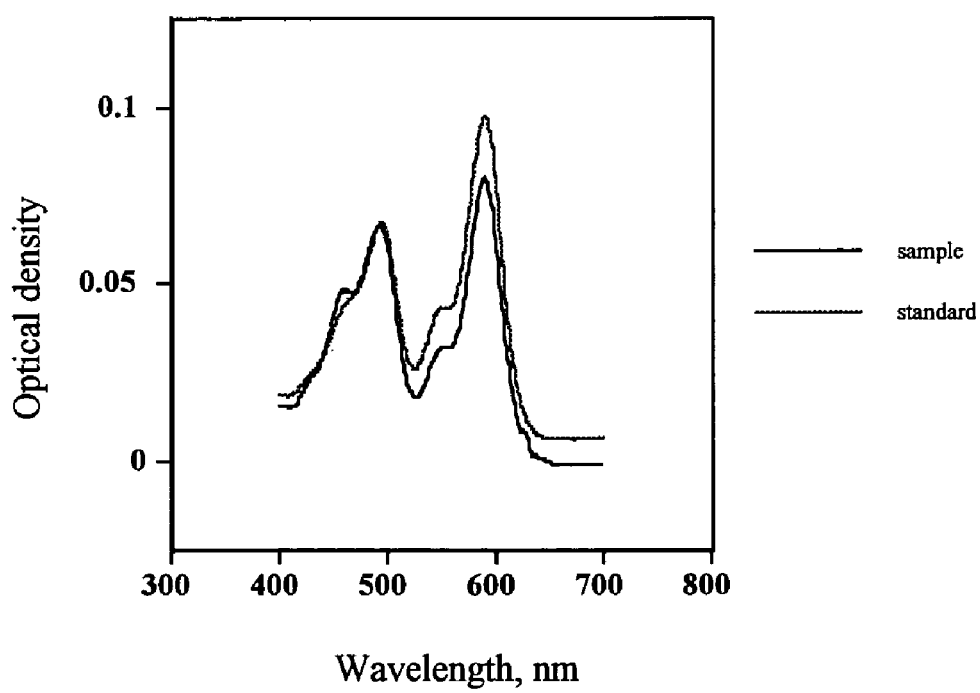

Stochiometry of Purified Particles: To study the stoichiometry of the recharged complexes, DNA, PLL and SPLL polymers were labeled with rhodamine and fluorescein moieties to yield Rh-DNA, Fl-PLL and Fl-SPLL with known degree of modification and adsorption coefficients respectively. Rh-DNA/Fl-PLL/SPLL and Rh-DNA/PLL/Fl-SPLL complexes were formed in low salt buffer and then separated from non-bound polyelectrolyte using density gradient ultracentrifugation. Corresponding amounts of each constituent can be determined by measuring optical density at 495 nm and 595 nm respectively. DNA complexes sediment through 10% sucrose solution and are retained in the separating layer between 10% sucrose and 40% metrizamide (metrizamide cushion). All Rh-DNA was found to be located on the sucrose/metrizamide border. Non-bound PLL and SPLL were found not to enter the 10% sucrose layer. DNA/PLL/SPLL complexes were found non-soluble and form precipitate on the density layer. The recovered complexes were solubilized in 2.5 M NaCl and their visible spectra were analyzed. FIG. 3 represents Rh-DNA/Fl-PLL/SPLL (FIG. 3a) and Rh-DNA/PLL/Fl-SPLL (FIG. 3b) complex spectra respectively together with standard Rh-DNA/Fl-PLL and Rh-DNA/Fl-SPLL (1:1) charge ratio mixtures. The data clearly indicates that precipitated complex contains all three polyelectrolytes with a stoichiometry of a 1:1:1 charge ratio.

Example 4

Zeta Potential of Purified Particles: As one may conclude from stoichiometry studies, the DNA/PLL/SPLL (1:3:10) initial mixture along with 7x excess of free SPLL also contains 2x excess of PLL/SPLL particles ("blank particles") not complexing DNA. These particles were found not to enter the 10% sucrose layer ensuring complete separation of DNA containing particles from PLL and SPLL excess. Zeta potential was measured using Brookhaven Instruments Corp. Zeta Plus Zeta Potential Analyzer. DNA concentration was 20 mg/ml in 1.5 ml of 25 mM HEPES, pH 7.5.

Example 5

Figure 4:
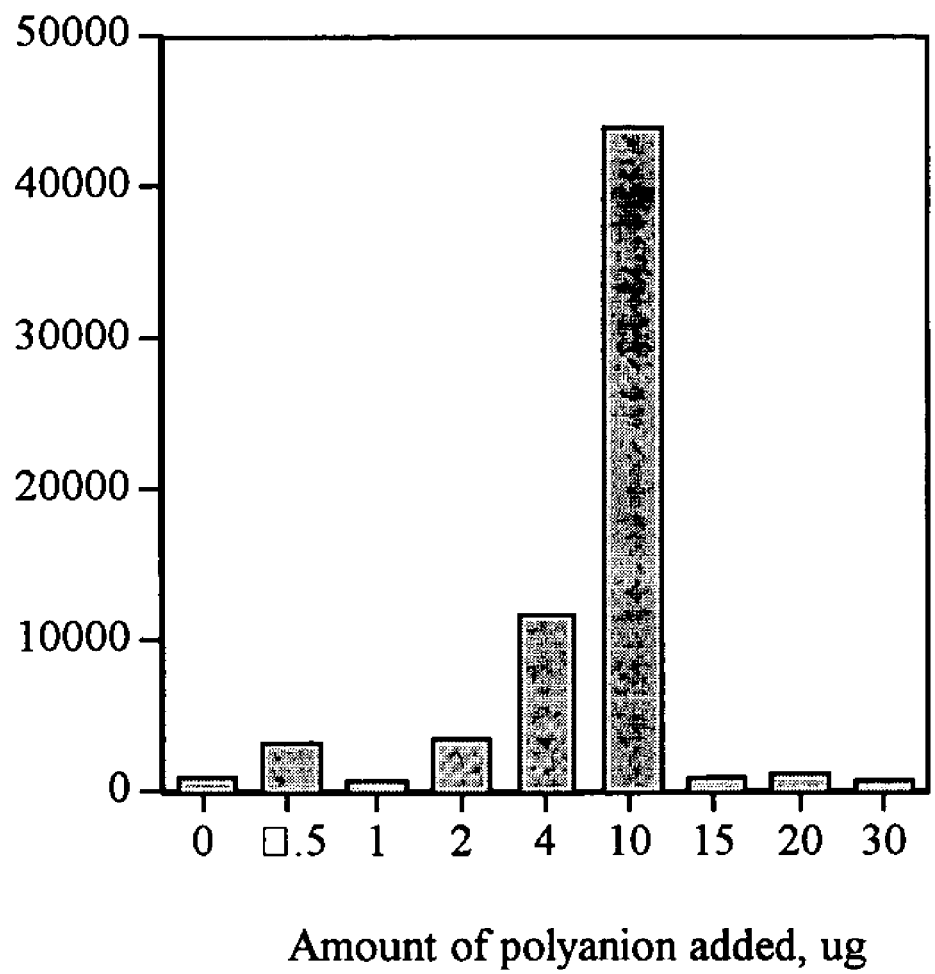
FIG. 4 illustrates transfection efficacy of DNA/PEI complexes recharged with increasing amounts of SPLL polyanion. DNA/PEI/SPLL complexes (2 micrograms DNA, 4 micrograms PEI) were added to HUH7 cells in bovine serum. After 4 hrs of incubation serum with DNA was replaced with fresh OPTI-MEM culture medium with 10% fetal serum. Cells were harvested for luciferase assay 48 hrs after transfection.

In vitro transfection enhancement upon recharging of DNA/polycation complexes. Recharging can increase the transfection activity of DNA/polycation complexes. FIG. 4 shows the results of transfection of HUH7 liver cells in 100% bovine serum with DNA/PEI (1:2 w/w) complexes recharged with increasing amounts of SPLL (Mw=460 kDa). At optimal SPLL concentration activity of recharged complex exceeds the activity of the non-recharged one approximately 40 times. For transfection of recharged complexes, 2 μg of the reporter plasmid pCILuc (expressing the firefly luciferase cDNA from the human immediate early CMV promoter) (Zhang, G., Vargo, D., Budker, V., Armstrong, N., Knechtle, S. & Wolff, J. Human Gene Therapy 8, 1763-1772 (1997)) was complexed with the polycation and polyanion in low salt buffer. Resulting complexes were added to 35 mm wells containing cells at about 60% confluence. Transfected cells were harvested 48 hours after transfection and cells were lysed and analyzed for luciferase activity using a Lumat LB 9507 luminometer (EG&G Berthold).

Example 6

Recharged DNA/PEI complexes have reduced toxicity and exhibit gene transfer activity in vivo in an organism. Recharging of DNA/polycation complexes with strong polyanions which help to release DNA can also make complexes less toxic in vivo. Resulting complexes also are active in gene transfer in lungs upon i/v administration in mice. Table 1 shows the toxicity of DNA/PEI/polyacrylic acid complex is decreasing with the increase of polyacrylic acid content. Tertiary DNA/PEI/polyacrylic acid complexes were formed in 290 mM glucose, 5 mM HEPES, pH 7.4 at DNA concentration of 0.2 mg/ml and PEI concentration of 0.4 mg/ml. Each animal was injected 0.25 ml of DNA complex solution. After 24 hours, the animals were sacrificed, lungs, livers, hearts, kidneys were removed and homogenized at 4° C. Luciferase activity of extracts (10 ul) was measured using a Lumat LB 9507 luminometer (EG&G Berthold).

TABLE 1

In vivo gene transfer activity in mouse organs upon i/v administration of DNA/PEI/polyacrylic acid complexes (50 micrograms/100 micrograms).

| | Amount of polyacrylic acid Added, (micrograms) | | | |
|---|---|---|---|---|
| | 40 | 50 | 60 | 70 |
| | Luciferase Activity, LU | | | |
| Liver | 1465 | 3266 | 14537 | 387 |
| Lung | 182187 | 9392 | 325 | 162335 |

TABLE 1-continued

In vivo gene transfer activity in mouse organs upon i/v administration of DNA/PEI/polyacrylic acid complexes (50 micrograms/100 micrograms).

| | Amount of polyacrylic acid Added, (micrograms) | | | |
|---|---|---|---|---|
| | 40 | 50 | 60 | 70 |
| | Luciferase Activity, LU | | | |
| Spleen | 3752 | 1925 | 1647 | 1307 |
| Heart | 2186 | 158 | 76 | 1262 |
| Animal Survival (dead/total) | 1/3 | 1/4 | 0/3 | 0/3 |

Example 7

Crosslinking of polycation and polyanion layers on the DNA-containing particles increases their stability in serum and on the cell surface.

Negatively charged (recharged) particles of condensed DNA can possess the same physico-chemical properties as positively charged (non-recharged) ones. This includes flocculation in high salt solutions (including physiologic concentration). We found that chemical crosslinking of cationic and anionic layers of the DNA particles can substantially improve stability of the particles in serum as well as on the cell surface. Table 2 shows the time course of unimodal particle size of DNA/PLL/SPLL crosslinked and non-crosslinked particles in 80% bovine serum as determined by dynamic light scattering.

TABLE 2

Particle sizing of DNA/PLL/SPLL crosslinked and non-crosslinked complexes in 80% serum.

| Time, min crosslinking | size (nm) no crosslinking | size (nm) |
|---|---|---|
| 0 | 153 | 104 |
| 15 | 154 | 105 |
| 60 | 171 | 108 |
| 200 | 246 | 115 |

Crosslinked particles essentially do not change their size in 200 min at room temperature while non-crosslinked control flocculates rapidly. Crosslinking with cleavable reagents might help to overcome an inactivity problem. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

Example 8

Pegylation of polyanions for recharging. Recharging of DNA/polycation particles with PEG-polyanion conjugates can substantially stabilize recharged particles against salt-induced flocculation. Preparation of PEG-SPLL conjugate. Water-soluble carbodiimide (EDC, 5 mg) and N-hydroxysulfosuccinimide (S-NHS, 10 mg) were added to the 0.25 ml solution of SPLL (20 mg/ml, Mw=210 kDa) at pH 5.0 and incubated for 5 min at room temperature. Monoamino-polyethyleneglycol (4 mg, 0.4 ml in 0.1 M HEPES, pH 8.0) was added to the SPLL and the mixture was continued to incubate for 1 more hour. PEG-SPLL conjugate was dialysed against deionized water overnight at 4° C. and freeze-dried. This preparation resulted in 5% (mol) substitution of COOH groups with PEG chains.

DNA-containing particles were prepared using the procedure in Example 1 with the exception that SPLL-PEG conjugate was doubled compared to SPLL. Table 3 shows the time course of unimodal particle size of DNA/PLL/SPLL and DNA/PLL/PEG-SPLL particles in 80% bovine serum as determined by dynamic light scattering. Pegylated particles exhibit higher stability towards flocculation as opposed to non-pegylate ones.

TABLE 3

Particle sizing of DNA/PLL/polyanion complexes recharged with SPLL and PEG-SPLL in 80% serum.

| Time, min | Size (nm) SPLL | Size (nm) PEG-SPLL |
|---|---|---|
| 0 | 441 | 118 |
| 15 | 750 | 118 |
| 60 | 2466 | 139 |
| 120 | 5494 | 116 |

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A tertiary complex for delivering a nucleic acid to a cell in vivo, comprising:
   a) the nucleic acid;
   b) a polycation polymer complexed with the nucleic acid; and,
   c) a polyanion polymer, having more than 80 monomer units, complexed with the polycation via ionic interaction, wherein the polyanion polymer is not the nucleic acid of a) and the polyanion and the polycation polymers comprise block co-polymers.

* * * * *